US009200993B2

(12) United States Patent
Chevalier, Jr. et al.

(10) Patent No.: US 9,200,993 B2
(45) Date of Patent: Dec. 1, 2015

(54) FLEXIBLE CONTAINER INSPECTION

(71) Applicant: Teledyne Instruments, Inc., Thousand Oaks, CA (US)

(72) Inventors: Robert A. Chevalier, Jr., East Falmouth, MA (US); Peter K. Novacon, Osterville, MA (US); Ryan D. Stirling, Mashpee, MA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 254 days.

(21) Appl. No.: 13/665,548

(22) Filed: Oct. 31, 2012

(65) Prior Publication Data

US 2013/0104664 A1 May 2, 2013

Related U.S. Application Data

(60) Provisional application No. 61/554,406, filed on Nov. 1, 2011.

(51) Int. Cl.
*G01B 11/16* (2006.01)
*G01N 3/08* (2006.01)
(Continued)

(52) U.S. Cl.
CPC ............... *G01N 3/08* (2013.01); *G01M 3/3218* (2013.01); *G01M 3/3272* (2013.01); *G01M 3/36* (2013.01); *G01N 2203/0206* (2013.01); *G01N 2203/0274* (2013.01)

(58) Field of Classification Search
CPC ... G01M 3/3218; G01M 3/36; G01M 3/3272; G01N 2203/0274; G01N 3/08; B30B 9/3082
USPC .................................... 73/763, 800, 818, 849
See application file for complete search history.

(56) References Cited

U.S. PATENT DOCUMENTS

| | | |
|---|---|---|
| 4,024,956 A | 5/1977 | Cassidy |
| 4,756,184 A | 7/1988 | Reishus et al. |

(Continued)

FOREIGN PATENT DOCUMENTS

| | | |
|---|---|---|
| DE | 196 48 778 A1 | 5/1998 |
| DE | 102005009918 A1 | 9/2006 |

(Continued)

OTHER PUBLICATIONS

Ayhan, Z. et al., "Inspection of Seal Integrity of Food Packages Using Ultrasound and Pressure Differential Techniques", Applied Engineering in Agriculture, Mar. 2001, vol. 17, No. 2, 16 pages.

(Continued)

*Primary Examiner* — Max Noori
(74) *Attorney, Agent, or Firm* — K&L Gates LLP

(57) ABSTRACT

An apparatus for testing flexible containers traveling along a production line is disclosed. The apparatus includes a compression assembly in line with the production line. The compression assembly has a flexible section for directly contacting and applying a predetermined compression over a predetermined distance to a plurality of containers as they travel by an inspection station. The apparatus also includes a sensor assembly provided in direct contact with a container while a container is in the inspection station. The sensor assembly is arranged to sense the force applied by the compression assembly to the container. The sensor assembly generates a signal that varies in accordance with the internal pressure of the containers as they pass by the sensor assembly. The apparatus further includes a processing circuit configured to receive the signals from the sensor assembly and to determine the acceptability of the internal pressure of the containers.

18 Claims, 8 Drawing Sheets

(51) Int. Cl.
*G01M 3/32* (2006.01)
*G01M 3/36* (2006.01)

(56) References Cited

U.S. PATENT DOCUMENTS

| | | | |
|---|---|---|---|
| 4,862,732 | A | 9/1989 | Raymond et al. |
| 4,864,848 | A | 9/1989 | Irvine |
| 4,898,023 | A | 2/1990 | Yamada et al. |
| 4,930,345 | A | 6/1990 | Bausch |
| 5,259,237 | A | 11/1993 | Aarts |
| 5,531,101 | A | 7/1996 | Fenlon |
| 5,767,392 | A | 6/1998 | Belcher et al. |
| 6,330,823 | B1 | 12/2001 | Raymond |
| 6,427,524 | B1 * | 8/2002 | Raspante et al. ............... 73/45.4 |
| 6,439,032 | B1 | 8/2002 | Lehmann |
| 6,666,071 | B1 * | 12/2003 | McCormick ................... 73/49.2 |
| 6,792,371 | B1 | 9/2004 | Turner |
| 6,918,285 | B2 * | 7/2005 | Chevalier et al. .............. 73/49.3 |
| 7,380,440 | B2 | 6/2008 | Lehmann |
| 7,779,674 | B2 | 8/2010 | Forestelli |
| 2007/0036686 | A1 * | 2/2007 | Hatamian et al. ............. 422/102 |
| 2011/0056275 | A1 | 3/2011 | Calhoun et al. |
| 2011/0127142 | A1 | 6/2011 | Weidman et al. |

FOREIGN PATENT DOCUMENTS

| | | |
|---|---|---|
| DE | 1020060 54 290 A1 | 5/2007 |
| WO | WO-02/073151 A1 | 9/2002 |
| WO | WO-2005/124308 A2 | 12/2005 |

OTHER PUBLICATIONS

Caporali, Ronald V. et al., "How Do Vacuum Pack Juice Containers Hold Up Under Internal Pressure?", Glass Industry, vol. 67, No. 2, Feb. 1986, 5 pages.

Kronberg, James W., "Method and Apparatus for Container Leakage Testing", dated Oct. 18, 1993, 15 pages.

Pascall, M. A., "Evaluation of a Laboratory-scale Pressure Differential (Force/decay) System for Non-destructive Leak Detection of Flexible and Semi-rigid Packaging", Packaging Technology and Science, vol. 15, No. 4, Jul./Aug. 2002, 12 pages.

Sivaramakrishna, Vijaykrishna et al., "PET Bottles Seal Quality Testing Using an On-line Pressure Differential Detector", Journal of Food Engineering, vol. 80, No. 2, May 2007, 10 pages.

Yam, Kit L., "On-Line Inspection System and Testing Method for Pouch Integrity", Final Technical Report, Report No. FTR 4.0, dated Jan. 1994, 117 pages.

International Search Report and Written Opinion for PCT Application No. PCT/US2012/062769, mail date Jan. 18, 2013, 7 pages.

\* cited by examiner

FLEXIBLE CONTAINER INSPECTION

CROSS-REFERENCE TO RELATED APPLICATION

This application claims the benefit of U.S. Provisional Application No. 61/554,406, filed Nov. 1, 2011, the entirety of which is hereby incorporated by reference.

BACKGROUND

This invention generally relates to apparatus and methods for testing flexible containers. More specifically, this invention relates to apparatus and methods for testing the seal integrity of containers and especially, but not exclusively, is intended for use in testing containers comprising a container body having an aperture or opening which is sealed by a flexible lid or cover.

In many industries, it is important to test the seal integrity of containers. For example, in the food industry, it is desirable to ensure that containers in which food products are packed are completely sealed to ensure that the contents are in good condition, free from molds, bacteria and other pathogenic organisms, so that they will be safe when used by consumers. The pharmaceutical industry similarly requires that containers for medications, especially solutions intended for injection or intravenous administration, be protected from contamination or serious danger to public health may result.

SUMMARY

One embodiment of the invention relates to an apparatus for testing flexible containers traveling along a production line. The apparatus includes a compression assembly in line with a production line. The compression assembly has a flexible section for directly contacting and applying a predetermined compression over a predetermined distance to a plurality of containers as they travel by an inspection station. The apparatus also includes a sensor assembly provided in direct contact with a container while a container is in the inspection station. The sensor assembly is fixed relative to the production line. The sensor assembly is arranged to sense the force applied by the compression assembly to the container. The sensor assembly generates a signal that varies in accordance with the internal pressure of the containers as they pass by the sensor assembly. The apparatus further includes a processing circuit configured to receive the signals from the sensor assembly and to determine the acceptability of the internal pressure of the containers.

Another embodiment of the invention relates to a method for testing flexible containers as they travel along a production line. The method includes applying a predetermined compression to a plurality of containers as they travel along the production line. The method also includes directly contacting the container with a sensor assembly to generate responses that vary in accordance with the internal pressure of the container as it passes by the sensor assembly while the predetermined compression is applied to each container. The sensor assembly is fixed relative to the production line. The method further includes analyzing the responses to determine the internal pressure in the containers.

BRIEF DESCRIPTION OF THE DRAWINGS

The structure, operation, and methodology of the invention, together with other objects and advantages thereof, may best be understood by reading the detailed description in conjunction with the drawings in which each part has an assigned numeral that identifies it wherever it appears in the various drawings.

DETAILED DESCRIPTION

The present disclosure generally relates to apparatus and methods for leak testing flexible containers such as those made of plastic and containing a substance that is typically sealed with the container by a closure such as a flexible top or lid formed of a flexible material such as a metallic foil or polymeric material. Typically, there is an air space above the top surface of the substance. With such containers, leaks can occur because of poor closure seals or the presence of holes in either the lid or walls of the container.

To test for such leaks, and for other defects or malfunctions such as over or under-filled containers, the apparatus utilizes a compression system that applies a predetermined compression force to the container as it travels along a predetermined path in-line and synchronized with the container production line so that containers need not be removed from production for testing purposes. While a container travels along the predetermined distance during which compression is applied, the displacement of the container (e.g., via the lid) is sensed by at least one test station to provide information about the internal pressure of the container at the station. The information generated is then passed to a computer or dedicated processor for purposes of analysis. After testing, containers that are found defective are removed from the production line (e.g., by any well-known manner).

One or more embodiments may provide high-speed apparatus and methods for leak testing containers without removing the containers from a production line. One example of such an embodiment includes an apparatus and method for in-line testing of the internal pressure of flexible containers traveling along a production line at high speeds. The apparatus inspects semi-rigid plastic and thin-walled containers filled with a substance by analyzing the output from a load cell that measures the reaction force applied to a container through a load cell roller while a flexible belt directly contacts containers while moving them through an inspection station without interrupting the flow of the production line.

Figure 1:
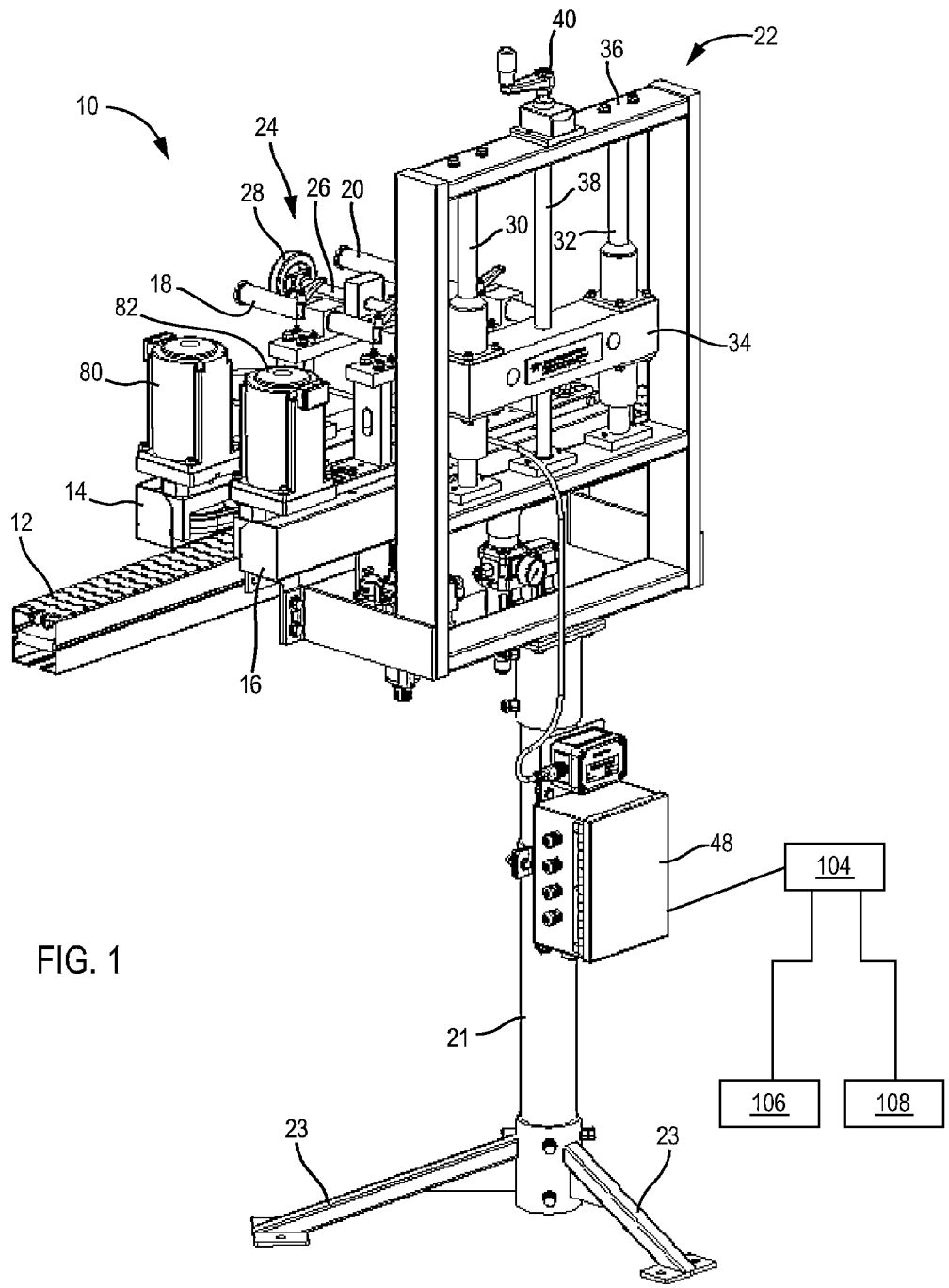
FIG. 1 is a rear perspective view of an apparatus positioned over a portion of a continuous conveyor for transporting containers along a production line as they undergo various manufacturing and testing operations.
Figure 2:
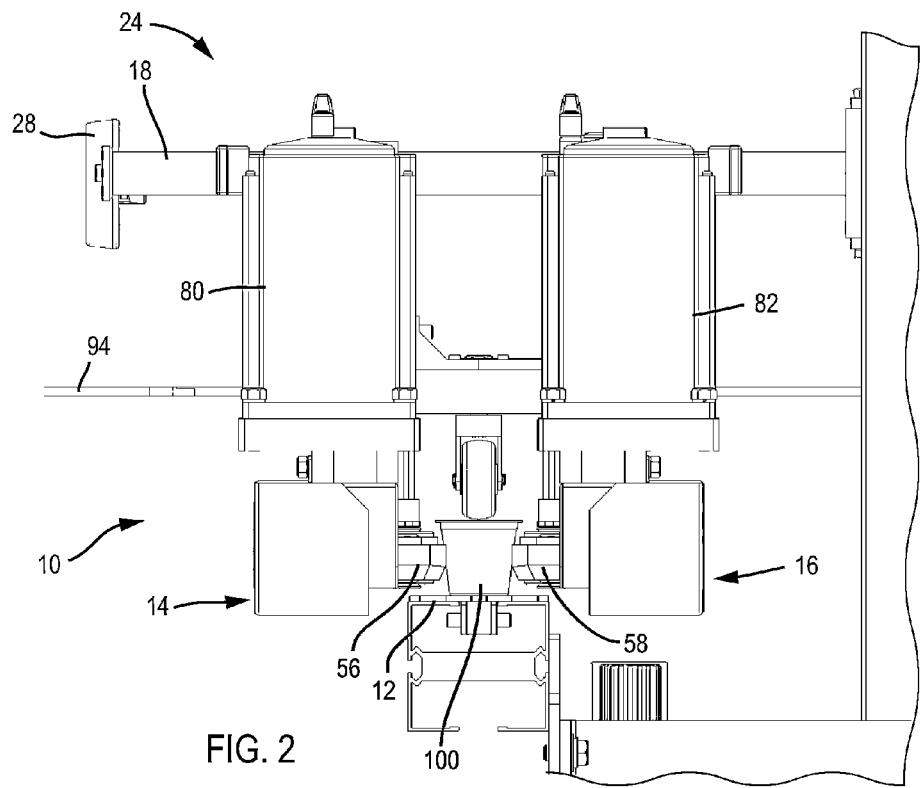
FIG. 2 is a rear elevation view of the apparatus of FIG. 1, showing a container being received between the compression elements and engaging an overhead sensor assembly.
Figure 3:
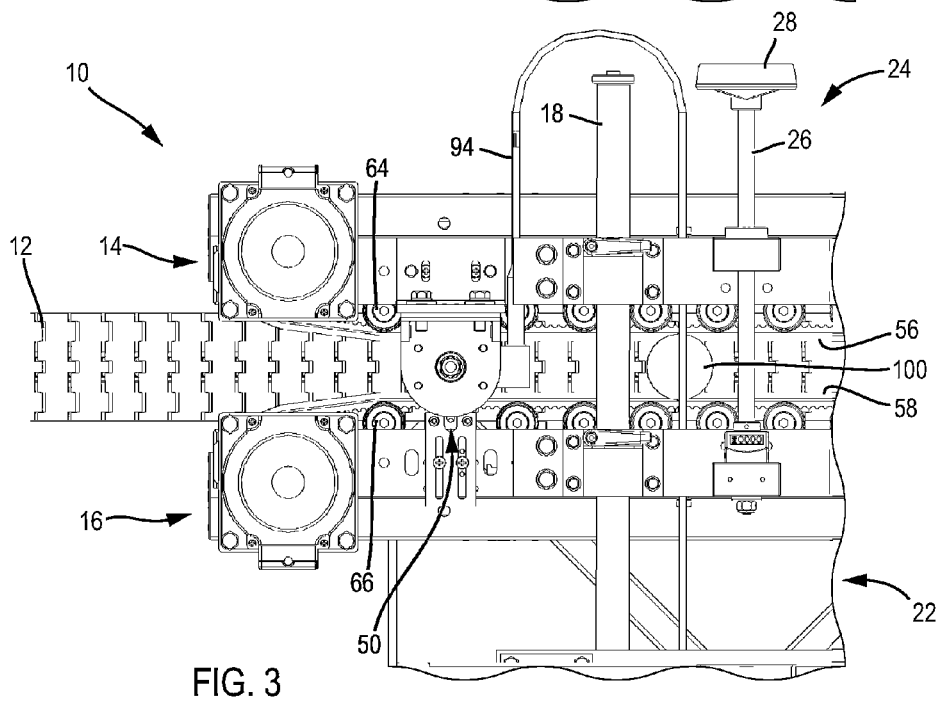
FIG. 3 is a top view of the apparatus of FIG. 1.

Referring now to FIGS. 1-3, a leak testing apparatus or system 10 is shown according to an exemplary embodiment. System 10 includes a frame that supports a pair of opposed compression assemblies 14 and 16. Compression assemblies 14 and 16 sit just above a production line 12 that feeds containers 100 between them. Only a segment of a production line 12 is shown, and those skilled in the art will appreciate that such production lines will run for significantly longer lengths both prior to and after system 10 in a fully implemented production environment. Because system 10 is a free standing, self contained apparatus and not directly coupled to production line 12, it may be moved to interact with different portions of production line 12.

While containers 100 will be described herein as containing a particulate substance such as coffee grounds, it should be understood that the containers may contain other substances, such as liquids, pressurized gasses, gels and solid-liquid mixtures, and the like. Further, the containers 100 may have a different shape, size, or construction as described herein and shown in the figures; for example, the containers may be bags (e.g., potato chip bag) or other type of container (e.g., baby food container, pet food container, yogurt container, etc.).

The compression assemblies 14 and 16 are supported by a support frame 22 that is configured to permit the height and width between compression assemblies 14 and 16 to be adjusted to fit the requirements of the production line and the size of the container which it is to test. As seen in FIG. 1, support frame 22 is a generally L-shaped assembly coupled to a base section having a post 21 with adjustable leveling feet 23. The support frame 22 also includes a vertical section that supports a compression assembly carriage 24. Mounted to the compression assembly carriage 24 are the pair of spaced apart compression assemblies 14 and 16. Compression assemblies 14 and 16 are mounted to the compression assembly carriage 24 via horizontally mounted cantilevered rods 18 and 20. The spacing between compression assemblies 14 and 16 may be adjusted to accommodate different sized containers 100 through the use of a spacing screw 26 that is operated by turning a spacing adjustment wheel 28. In this connection, spacing screw 26 is provided with two screw sections that are oppositely threaded while one of them is connected to compression assembly carriage 24 at its root by a slip joint so that both compression assemblies 14 and 16 move toward and away from one another by equal amounts as spacing adjustment wheel 28 is rotated.

Referring to FIG. 1, the vertical height of compression assemblies 14 and 16 may also be adjusted to accommodate containers 100 of different heights by moving compression assembly carriage 24 up and down. Compression assembly carriage 24 is slidably mounted to a pair of vertically extending carriage guide rods 30 and 32 that are, in turn, fixedly mounted between a pair of horizontally-oriented cross members 34 and 36 that form part of the vertically extending section of support frame 22. A height adjust threaded rod 38 passes through a flanged portion of compression assembly carriage 24 and turns in response to turning a height adjustment wheel 40. Height locking features such as knobs may be provided to release compression assembly carriage 24 so that its height may be changed and to lock it in place after adjustment to the desired height has been completed.

Compression assemblies 14 and 16 may be slidably mounted to horizontal guide rods 18 and 20 via guide blocks, each of which is provided with locking features such as knobs to fix these assemblies in place once adjusted by spacing adjustment screw 26.

Figure 13:
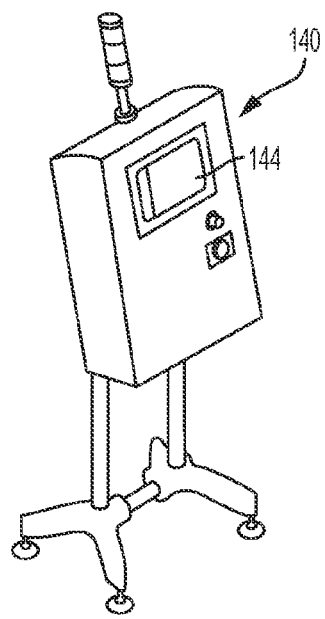
FIG. 13 is a pictorial representation of a control box having a user interface screen according to an exemplary embodiment.
Figure 14:
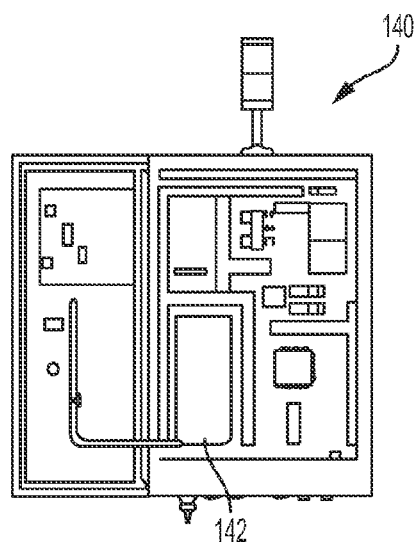
FIG. 14 is a pictorial representation of the interior of the control box of FIG. 13 having a digital signal processor (DSP) according to an exemplary embodiment.
Figure 15:
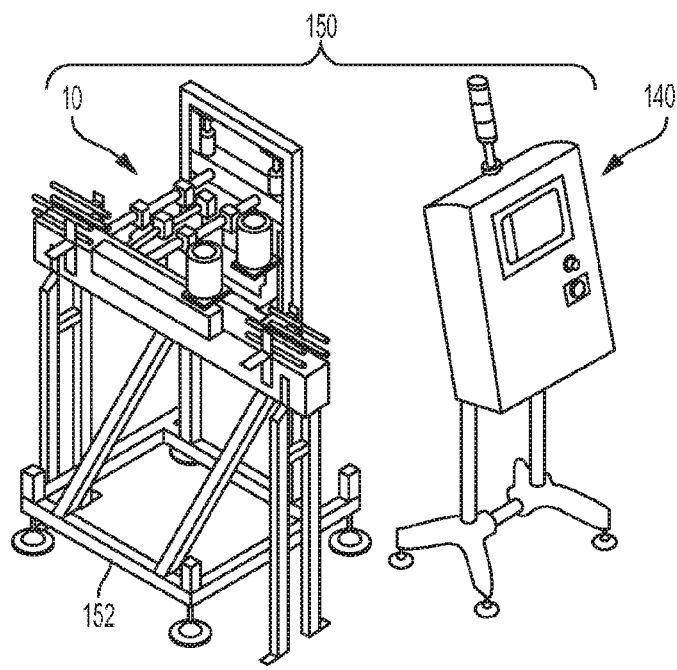
FIG. 15 is a pictorial representation of an inspection system according to an exemplary embodiment.

A motor speed controller may be provided for adjusting the speed of a pair of drive motors 80 and 82. System 10 further includes a junction box 48 that serves as a common point for connecting a variety of electrical subsystems of system 10, including controllers and data processing components (e.g., as contained in the control box as shown in FIGS. 13-15). According to an exemplary embodiment, information from an encoded drive shaft of the transport conveyor of the production line 12 may be fed into the system 10 (e.g., via junction box 48). System 10 can then control the spend of drive motors 80 and 82 (e.g., via the motor speed controller) to match the speed of compression assemblies 14 and 16 to that of the production line 12.

Figure 4:
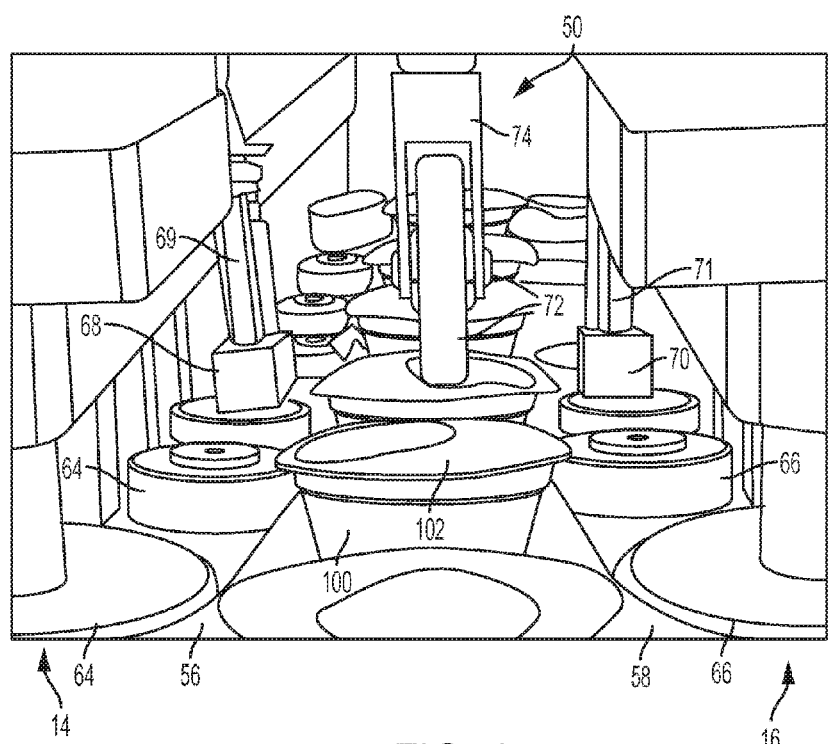
FIG. 4 is a perspective view of a plurality of containers being conveyed between the compression assemblies of the apparatus of FIG. 1.

Referring now to FIG. 4, a series of containers 100 are tested as they pass through system 10. The containers are passed through system 10 by a pair of spaced apart rotating conveyor belts 56 and 58 that form part of compression assemblies 14 and 16, respectively. Conveyor belts 56 and 58 are nominally parallel and one or both of conveyor belts 56 and 58 is intentionally set slightly into the path of travel of containers 100 as explained more fully below. At the front of in-feed end of system 10, conveyor belts 56 and 58 are supported by idler wheels 60 (shown in FIG. 5) that are mounted for movement with respect to their corresponding compression assemblies so that the tension in conveyor belts 56 and 58 may be adjusted as needed. Conveyor belts 56 and 58 are supported by vertically spaced rollers 64 and 66, respectively. The drive motors 80 and 82 are connected with drive wheels 84 and 86 that in turn are in friction contact with conveyor belts 58 and 56, respectively. The speed of conveyor belts 56 and 58 are synchronized to the container transportation conveyor of production line 12 to provide smooth container inspection without tipping containers over or slowing the manufacturing line. For instance, drive motors 80 and 82 may have encoded drive shafts that may be synched with the production line, allowing conveyors belts 56 and 58 to match speeds and start and stop simultaneously with production line 12.

An overhead sensor assembly 50 is disposed above production line 12 between compression assemblies 14 and 16. Overhead sensor assembly 50 is coupled to compression assembly 14, as described in detail below. A trigger system shown as a photosensor 68 and a trigger reflector 70 are coupled to compression assemblies 14 and 16 with supports 69 and 71, respectively. Photosensor 68 passes signals to a digital signal processor board (see 104 in FIG. 1) indicating when a container 100 is in place relative to sensor assembly 50 and load information is to be taken and recorded. Other trigger systems may be used, as is known in the art. Overhead sensor assembly and photosensor 68 may communicate with digital signal processor board 104 via a signal cable 94.

Figure 10:
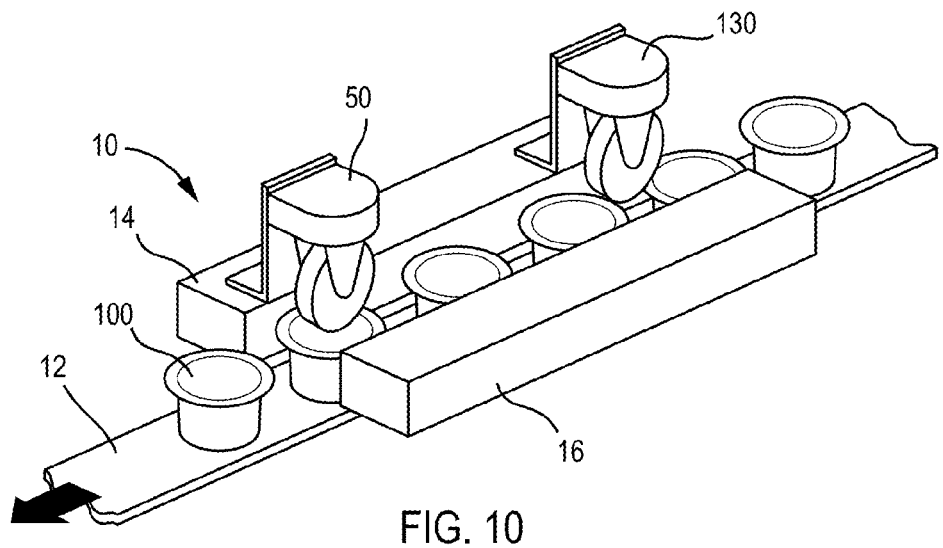
FIG. 10 is a schematic drawing of an apparatus including two overhead sensor assemblies.

Rollers 64, which are positioned directly opposite rollers 66 (as seen in FIG. 4), are positioned to protrude slightly into the path of travel of oncoming containers 100 so that the containers 100 are gently squeezed by conveyor belts 56 and 58 along a path of travel of the containers. According to one exemplary embodiment, the conveyor belts 56 and 58 apply a compression force that is substantially constant along the path of travel of the containers 100. In this embodiment, the overhead sensor assembly 50 is typically provided either at or near the end of the conveyor belts 56 and 58 (e.g., as shown in FIGS. 1-7), or at or near both the beginning and end of the conveyor belts 56 and 58 (e.g., as shown in FIG. 10). According to another exemplary embodiment, the space between conveyor belts 56 and 58 gradually decreases until the midpoint of a container 100 is nominally aligned with overhead sensor assembly 50, after which the spacing gradually increases again. In this embodiment, the overhead sensor assembly 50 is typically provided at or near a midpoint of the conveyor belts 56 and 58. As described above, container 100 is closed with a flexible cover or lid 102. According to one exemplary embodiment, lid 102 may be formed of a metallic foil. According to other exemplary embodiments, lid 102 may be another flexible material, such as a polymer film (e.g., a polyester film, etc.). Lid 102 may be domed when the container 100 is under compression (e.g., squeezed by belts 56 and 58).

As container 100 is squeezed between compression assemblies 14 and 16, the contents of container 100 are forced upward. If a proper seal is formed between lid 102 and container 100, the compression of container 100 will cause lid 102 to bulge or deflect upward. If an improper seal is formed between container 100 and lid 102, or if a leak exists in either container 100 or lid 102, air in container 100 will be allowed to escape as container 100 is compressed and lid 102 will be deflected a lesser amount or not at all. During this process, the upward deflection of lid 102 is transferred to a load cell 74 in sensor assembly 50 through the intermediary member of a roller wheel 72.

In other exemplary embodiments, container 100 may not include a lid 102. Instead, container 100 may be a bag formed of a flexible material such as a metallic foil, a polymer sheet, paper, or a foil-backed polymer or paper. Compression assemblies 14 and 16 may squeeze such a bag in one direction, with sensor assembly 50 detecting the resulting deformation of the bag in another direction (e.g., in a direction perpendicular to the direction of compression).

Neither rollers 64 nor rollers 66, which are typically made of metal, directly contact a container 100. Instead, containers 100 are contacted by the relatively wider and more flexible conveyor belts 56 and 58. Thus, containers 100 are gently squeezed by belts 56 and 58 (e.g., either with a constant pressure or a gradual pressure, as described above) and are never directly contacted by hard rollers that may otherwise damage them.

Figure 5:
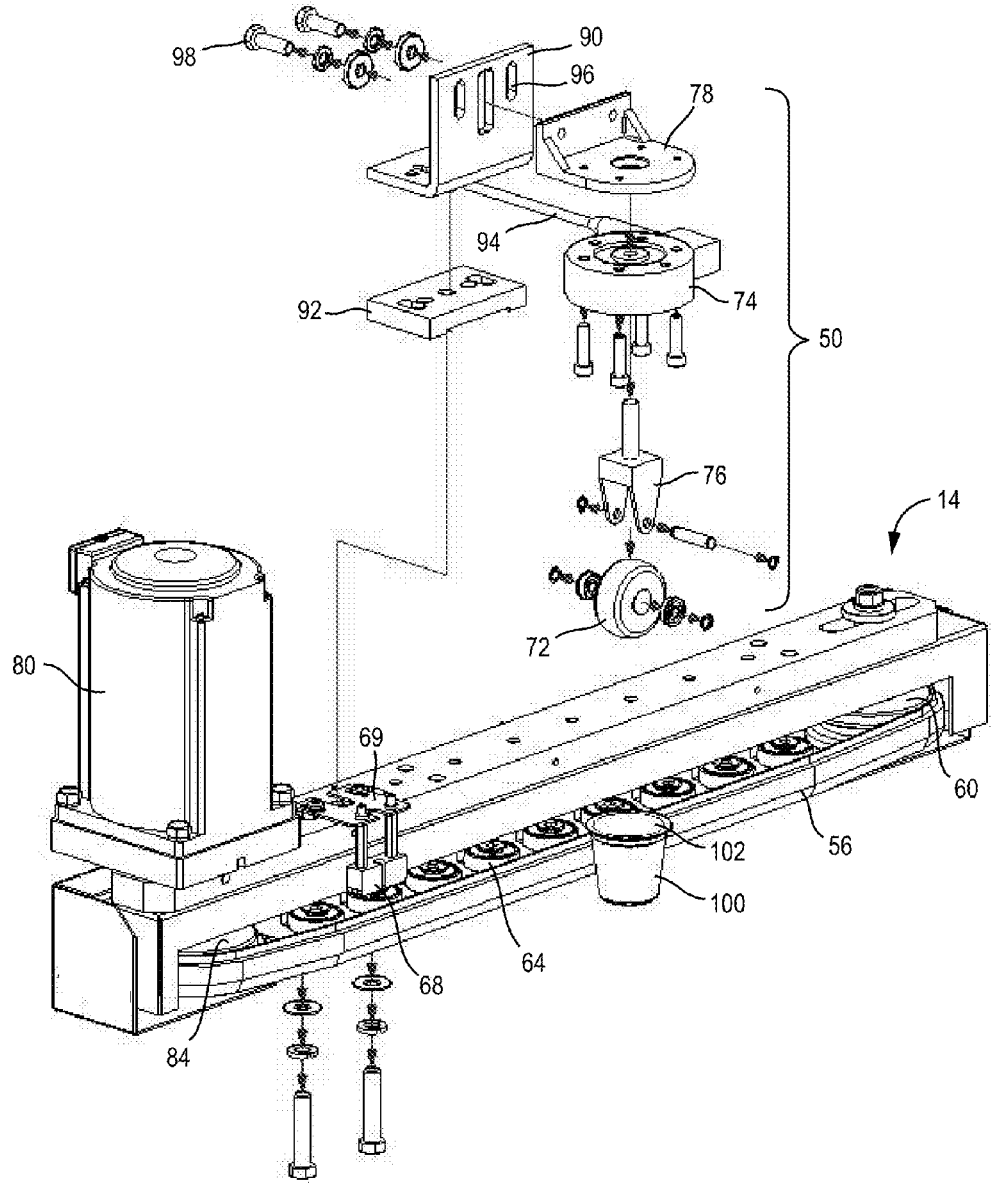
FIG. 5 is an exploded view of the overhead sensor assembly of the apparatus of FIG. 1.
Figure 6:
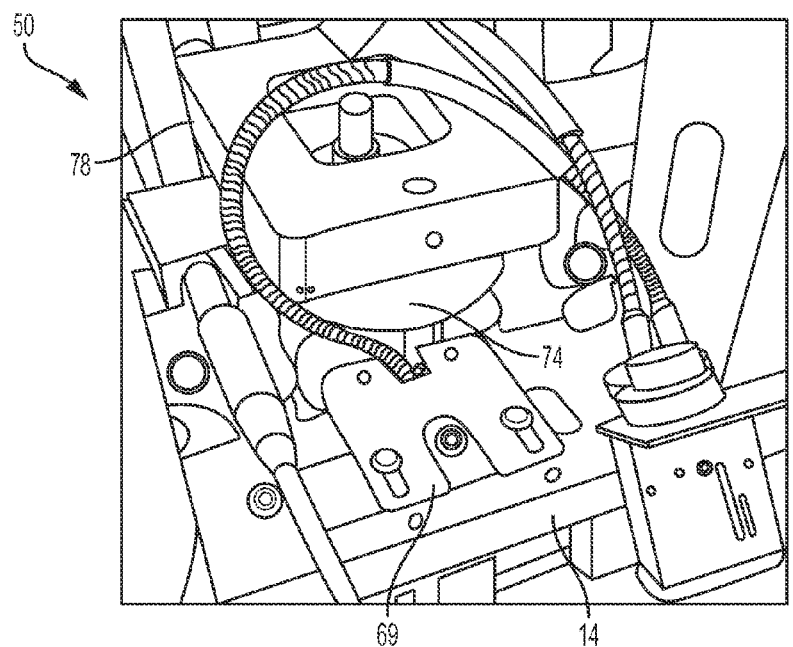
FIG. 6 is a perspective view of a typical load cell for the overhead sensor assembly of FIG. 5.
Figure 7:
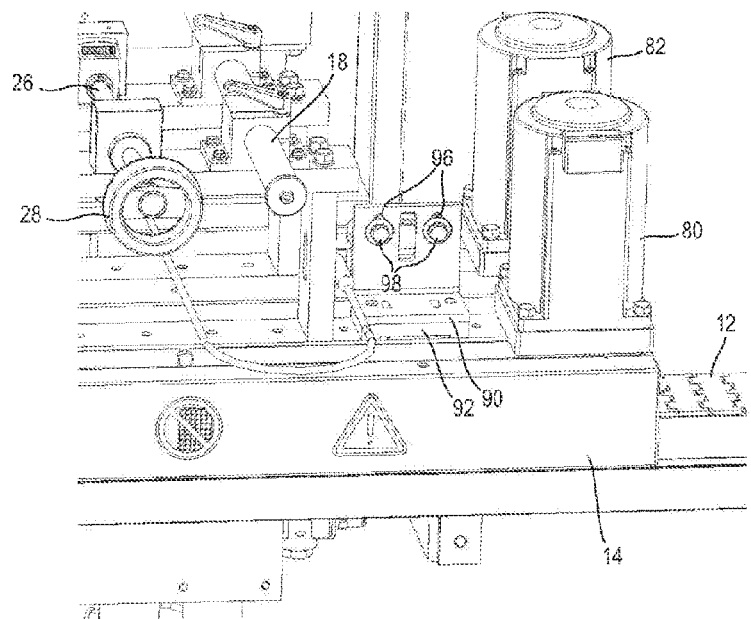
FIG. 7 is a perspective view of a mounting plate for an overhead sensor of FIG. 5.

Referring now to FIGS. 5-7, overhead sensor assembly 50 is shown according to an exemplary embodiment. As mentioned, sensor assembly includes a roller wheel 72 that contacts lid 102 of a container 100 being tested. Roller 72 is coupled to load cell 74 via a bracket 76 that allows roller 72 to rotate about a generally horizontal axis perpendicular to the path of containers 100 as they pass below sensor assembly 50 along production line 12. According to an exemplary embodiment, the width of roller wheel 72 is between 25% and 75% of the diameter of container 100. According to a preferred embodiment, the width of roller wheel 72 is between 30% and 50% of the diameter of container 100.

Load cell 74 is rigidly supported above production line through the interconnection of a load cell mount 78, a load cell assembly bracket 90, and a spacer 92. Load cell mount 78 and load cell assembly bracket 90 are each generally L-shaped brackets that are coupled together with fasteners 98 (e.g., threaded fasteners such as bolts). Bracket 90 and spacer 92 are, in turn, coupled to compression assembly 14. According to an exemplary embodiment, spacer 92 may not be required.

The height of roller wheel 72 above production line 12 may be adjusted in various ways to accommodate containers 100 of varied heights. For instance, fasteners 98 pass through slots 96 in bracket 90, allowing the vertical position of mount 78, load cell 74, bracket 76, and roller wheel 72 to be adjusted relative to load cell assembly bracket 90. Further, spacer 92 may be replaced by a spacer with a greater or lesser thickness. Additionally, adjustable mounting screws (not shown) may be used to adjust the height (e.g., vertical height) of the roller wheel 72. Mount 78, bracket 90, and spacer 92 provide a rigid mounting structure for load cell 74 to substantially minimize the deflection of load cell 74 as roller wheel 72 is deflected by lid 102. The height of roller wheel 72 above production line 12 may also be adjusted with a change in the height of compression assemblies 14 and 16 (e.g., for testing containers of different heights).

Existing measurement systems may utilize load cells coupled to one of the sets of rollers 64 or 66. In such existing systems, the reaction load of the container (e.g., the sidewall of the container) is transferred to a load cell through the intermediary of a relatively flexible conveyor belt 56 or 58. Such a side-oriented load cell must therefore compensate for greater forces and the expected compression of the flexible conveyer belt. As such, a load cell for measuring the reaction load of container 100 may have a load capacity of as much as 50 lbs or greater.

By contrast, in the overhead sensor assembly 50, an upward force due to the deflection of lid 102 is transferred to load cell 74 through a generally rigid path via roller wheel 72 and bracket 76. In addition, the upward deflection of lid 102 is relatively low, even if the container is free of leaks and is neither under-filled nor over-filled. Load cell 74 for an overhead sensor assembly 50 may therefore be a low capacity load cell 74 with a higher resolution. According to an exemplary embodiment, load cell 74 is a standard 10 lb load cell calibrated to 5 psi. According to an exemplary embodiment, load cell 74 is a generally cylindrical, pancake-type load cell. In other exemplary embodiments, the sensor assembly 50 may include another suitable load cell, such as a beam-type load cell.

Load cells 74 and roller wheels 72 of various physical dimensions and properties may be utilized to improve various aspects of the measurements of containers 100. For instance, increasing the width of roller wheel 72 increases the contact area between lid 102 and roller wheel 72. The greater contact area increases the amount of pressure applied to roller wheel 72 and, in turn, to load cell 74, without increasing the amount of force transferred to the lid of the container (such that the lid of the container is free from being damaged by the roller). Reducing the size of load cell 74 improves the range and resolution of load cell 74 (e.g., to detect small leaks or micro leaks).

According to an exemplary embodiment, the various components of the system 10 are constructed from suitable materials. For example, the roller wheel 72 may be formed of a relatively rigid material having low water absorption and low friction properties, such as an ABS polymer or acetal, such as Delrin®, which is commercially available from E. I. du Pont de Nemours and Company. Additionally, the brackets 76, 90 and mount 78 are formed from a highly rigid and corrosive-resistant material such as stainless steel. Also, the spacer 92 may be constructed from a polymer or metallic material.

Trigger photosensor 68 in conjunction with trigger reflector 70 operate to detect the presence of a container 100 proximate sensor assembly 50. Signals from the trigger photosensor 68 and load cell 74 are fed to a digital signal processor board 104 that is configured to collect and analyze data. Photosensor 68 is utilized to begin data collection with load cell 74 as the leading edge of container 100 contacts roller wheel 72 and end data collection with load cell 74 as roller wheel 72 loses contact with the trailing edge of container 100. According to an exemplary embodiment, photosensor 68 is coupled to compression assembly 14 approximately 18" "upstream" or towards the in-feed end of system 10 relative to the axis of roller wheel 72.

Photosensor 68 generates a preferably polarized beam that ordinarily is retroreflected by trigger reflector 70 when no portion of a container 100 is present to interrupt it. However, when any portion of a container interrupts the beam, a signal is generated to alert the digital signal processor 104 that a container is present and data is to be collected. The beam is preferably polarized to avoid passing light straight through containers that may be transparent to the beam.

A computer 106 may be integrated with system 10 and be provided with suitable software to facilitate data processing and analysis, provide a graphical user interface for an operator (e.g., as shown in FIGS. 13 and 15), display, print and store data, and perform general housekeeping functions. In this connection, it will be recognized that computer 106 may take on the functions of digital signal processor (DSP) board 104 when its software is appropriately configured and a suitable interface board is provided.

Figure 9:
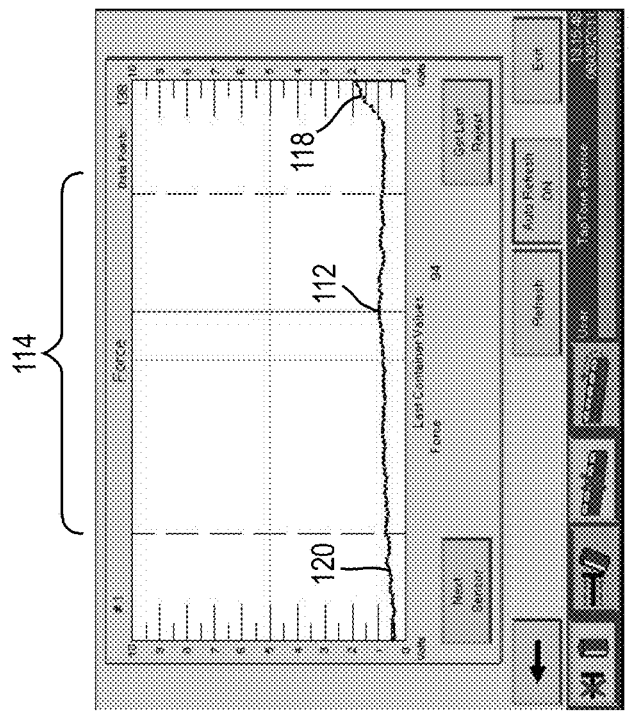
FIG. 9 is a graph showing the response of a sensor to a container with a known leak.
Figure 8:
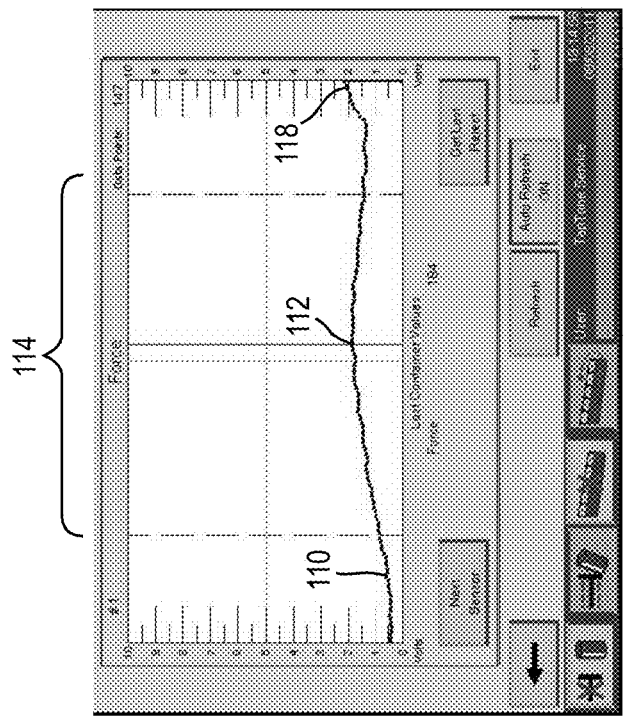
FIG. 8 is a graph showing the response of a sensor to a container with no leaks.

Referring now to FIGS. 8-9, a graph illustrating load cell response curves for an exemplary container 100 is shown for both a normal or leak-free scenario and for a low-pressure scenario caused by a leak. As seen in FIG. 8, load cell 74 generates an output voltage proportional to the force transferred to it via roller wheel 72 and bracket 76. Load cell 74 is configured to normally continuously output data but that data is sampled only during the trigger period defined as the time a container 100 is blocking the photosensor 68 as a container 100 passes under sensor assembly 50. A typical trigger period may be, for example, 105-175 milliseconds, while typical conveyor speeds may be, for example, 0-300 feet per minute.

The internal pressure of a container 100 is transferred through roller wheel 72 and bracket 76 to load cell 74. The electrical output of load cell 74 is conditioned for both gain and offset and then sent to an A/D converter located on data signal processor board 104. The digital signal is then processed to preferably find the maximum peak voltage 112, which is proportional to the internal pressure in container 100. FIG. 8 shows a force signal curve 110 for an exemplary normal container 100 while FIG. 9 shows a force signal curve 120 for the same type of container 100 with low internal pressure (e.g., because of an under-fill condition or a leak).

Referring to FIG. 8, the curve 110 for a normal container has a characteristic bell shape, gradually increasing, then rising along a more or less straight slope to a transition region where the slope decreases until a maximum or peak is reached. After the maximum, the remainder of the curve 110 is nominally the mirror image of its transit to maximum, although in practice there may be some asymmetries encountered. The peak voltage 112 of force curve 110 is determined from the collected data resident within a "Midpoint %" or data analysis window 114 defined as a percentage of the total trigger period. This peak voltage 112 is then scaled and a relative merit value is assigned to a container. The assigned merit value is then compared against user set rejection limits. Referring now to FIG. 9, a curve 120 for a container with low internal pressure does not show a characteristic bell-shaped curve. Curve 120 shows a minimal pressure rise with a low merit value. If the merit value is outside upper or lower reject limits, then that container is removed from the manufacturing line transportation conveyor by rejecter system 108 (see FIG. 1). Such a rejecter system 108 may be any device or system that suitably removes the faulty container (e.g., a mechanical arm, compressed air, a diverter, etc.).

Curve 110 or curve 120 may include peaks or spikes 118 near the beginning or end of the curve. Such a spike 118 may be the result of roller wheel 72 contacting the rim of container 100. The occurrence of spikes 118 can be reduced by adjusting the height of roller wheel 72 relative to production line 12.

A curve may indicate a false acceptance if the container being measured is overfilled. Such an overfill situation may be compensated for by adjusting the height of roller wheel 72 relative to production line 12.

An operator interface is preferably provided via computer 106 operating with a graphical user interface and equipped with software to permit setup, control data processing and collection, set and monitor acceptance limits, access manufacturing trends, perform control functions, and collect and display historical statistical data.

In addition, it will be apparent that other characteristics of the load cell force curves may be exploited as an adjunct to determining the acceptability of container performance. It will also be apparent that a number of mathematical algorithms may be used to calculate the maximum value. Disclosed here is one method of comparing sampled values during the Midpoint % and storing the maximum. The computer or processing circuit may be configured to determine the acceptability of container performance in any number of ways, for example, by determining whether the sensed pressure exceeds a threshold, by determining whether the sensed pressure exceeds a threshold for a predetermined period of time, by filtering the received data to account for noise or other factors, etc. An acceptable performance threshold may be pre-stored or programmed by a user or system operator.

Figure 11:
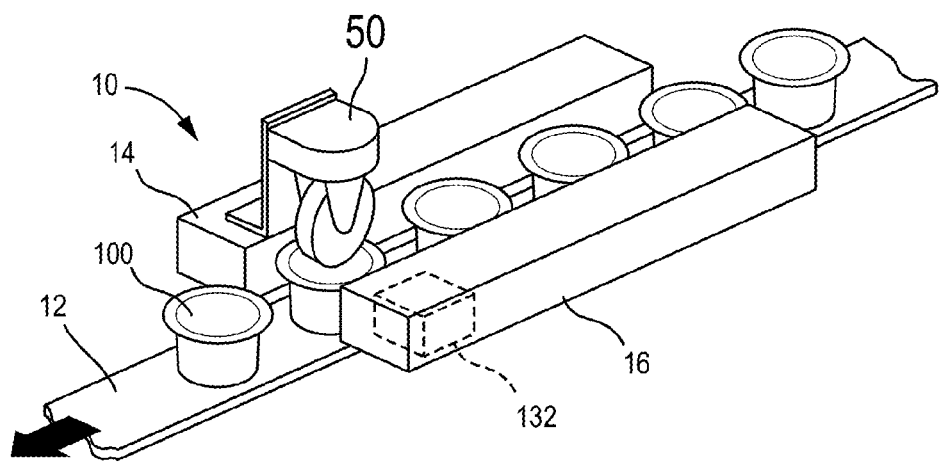
FIG. 11 is a schematic drawing of an apparatus including a side-mounted sensor proximate to an overhead sensor assembly.
Figure 12:
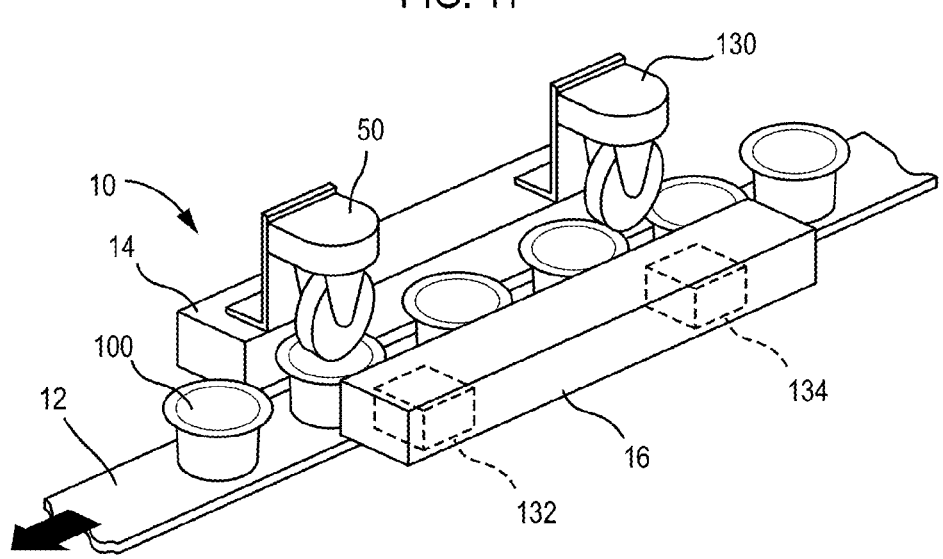
FIG. 12 is a schematic drawing of an apparatus including two side-mounted sensors and two overhead sensor assemblies.

While only one load cell has been shown as a preference, it will apparent to those skilled in the art that more than one load cell may be beneficially used to generate information about container pressures and other properties. FIGS. 10-12 illustrate schematic representations of systems 10 with various alternate arrangements of pressure sensor assemblies.

For instance, according to another exemplary embodiment as shown in FIG. 10, system 10 may include a second overhead sensor assembly 130. First overhead sensor system 50 may be provided near the rear of system 10 while the second overhead sensor assembly 130 may be provided proximate to the in-feed or front end of system 10. The data collected from overhead sensor assemblies 50 and 130 can be used to further diagnose potential malfunctions in the containers 100. While sensor assemblies 50 and 130 may each record a curve indicating a normal container similar to curve 110 in FIG. 8, the maximum peak voltage recorded by the rear sensor assembly 50 may be lower than the maximum peak voltage recorded by the front sensor assembly 130, indicating a possible slow, micro leak in the container. Thus, the value (e.g., maximum peak voltage) obtained from the first overhead sensor assembly 50 can be compared (e.g., difference, average, etc.) with the value (e.g., maximum peak voltage) of the second sensor assembly 130 to determine if there is a malfunction of the container/lid. For example, a third value based on the value from the first overhead sensor assembly 50 and the value from the second sensor assembly 130 can be obtained for determining if a malfunction has occurred.

According to another exemplary embodiment shown in FIG. 11, system 10 may include a load sensor 132 coupled to the rollers of compression assembly 14 or 16 proximate to overhead sensor assembly 50. Such a side mounted sensor 132 may be similar to a sensor as described in U.S. patent application Ser. No. 10/770,058, now issued as U.S. Pat. No. 6,918,285. The entire disclosure of U.S. patent application Ser. No. 10/770,058 (U.S. Pat. No. 6,918,285), is hereby incorporated by reference for all purposes.

According to another exemplary embodiment shown in FIG. 12, system 10 may include a first side mounted sensor 132 proximate to an overhead sensor assembly 50 provided near the rear of system 10 and a second side mounted sensor 134 proximate to a second overhead sensor assembly 130 provided near the in-feed or front end of system 10.

In each of the embodiments shown in FIGS. 11 and 12, the maximum peak voltage value (e.g., merit value) from each sensor assembly may be compared with the maximum peak voltage value (e.g., merit value) from another sensor assembly (e.g., to come up with a further value) for determining if a malfunction of the container/lid has occurred.

In still other exemplary embodiments, compression assemblies 14 and 16 may exert a vertical force on containers 100. Such a container 100 may be a bag, as described above, or may be a container with a lid 102 laying on a side (e.g., oriented sideways). Sensor assembly 50 is likewise oriented horizontally to detect the resulting horizontal deflection of container 100 or lid 102.

Referring now to FIGS. 13-14, a control box 140 for use with system 10 is shown according to an exemplary embodiment. The control box 140 includes the necessary components for controlling the system 10. For example, the control box includes a DSP board 142. The control box 140 may also include a user interface, such as the user interface screen 144 as shown in FIG. 13. According to one exemplary embodiment, the user interface is a touch screen 144 configured to allow a user to interact with the system 10. According to an exemplary embodiment, the control box 140 may be coupled to the junction box 48 via an electrical or communication cable.

Referring now to FIG. 15, the complete system 150 is shown according to an exemplary embodiment. Additionally, as shown in FIG. 15, system 10 includes an alternative base 152 and leveling system. The base 152 comprises a framework of members having a generally rectangular form, with a leveling leg coupled at each corner of the framework. The base 152 may also include diagonal support members as shown in FIG. 15.

The term processing circuit encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures. The processing circuit may be arranged in one or more modules (e.g., a sensing module, a calculating module, an output or display signal generating module, etc.) representing programmed portions of a computing device, which may comprise any analog and/or digital components configured to perform the functions recited herein.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the systems and methods shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. An apparatus for testing flexible containers traveling along a production line, the apparatus comprising:
    a compression assembly in line with the production line, the compression assembly having a flexible section for directly contacting and applying a predetermined compression over a predetermined distance to a plurality of containers as they travel by an inspection station;
    a sensor assembly comprising a load cell roller provided in direct contact with a flexible lid of a container while the container is in the inspection station, wherein the sensor assembly is fixed relative to the production line, the sensor assembly being arranged to sense the force applied by the compression assembly to the container, the sensor assembly generating a signal that varies in accordance with the internal pressure of the containers as they pass by the sensor assembly; and a processing circuit configured to receive the signals from the sensor assembly and to determine the acceptability of the internal pressure of the containers;

wherein the sensor assembly is configured to contact the flexible lid of each of the plurality of containers for detecting the internal pressure of the containers;

wherein the load cell roller of the sensor assembly directly contacts the flexible lid of the container and the sensor assembly further comprises a load cell directly in contact with the roller so that loads imposed on the roller from the flexible lid of the container are directly transferred to the load cell.

2. The apparatus of claim 1 wherein the compression assembly comprises a pair of spaced apart continuous loop belts that are arranged to hold the plurality of containers there between and to move the plurality of containers along the production line without interrupting their flow while applying the predetermined compression to the plurality of containers.

3. The apparatus of claim 2 further comprising an adjustment mechanism for adjusting the spacing between the compression assembly to allow the apparatus to operate on containers of differing sizes.

4. The apparatus of claim 1 wherein the load cell comprises a pancake load cell.

5. The apparatus of claim 1 further comprising a container detection circuit configured to detect when one of the plurality of containers is in a predetermined position with respect to the sensor.

6. The apparatus of claim 5 wherein the container detection circuit comprises a light source arranged to generate light and direct a beam of light towards the containers, and light detection circuit configured to detect when the beam is interrupted by, or reflected from, a container.

7. The apparatus of claim 1 wherein the processing circuit is arranged to detect, in the response from the sensor assembly, the peak pressure generated within each container caused by the predetermined compression and to measure the pressure within the container at a number of points on each side of the peak pressure.

8. The apparatus of claim 7 wherein the processing circuit is arranged to generate an output signal if the peak pressure generated within each container lies outside a predetermined range.

9. The apparatus of claim 1 having the form of a mobile unit capable of being added to an existing production line, the apparatus having a support means capable of supporting the compression assembly and the sensor assembly separately from the production line.

10. A method for testing flexible containers as they travel along a production line, the method comprising:
    applying a predetermined compression to a plurality of containers as they travel along the production line;
    detecting the internal pressure of the containers by directly contacting a flexible lid of the container with a sensor assembly comprising a load cell roller and a load cell to generate responses that vary in accordance with the internal pressure of the container as it passes by the sensor assembly while the predetermined compression is applied to each container, wherein the sensor assembly is fixed relative to the production line; and
    analyzing the responses to determine the internal pressure in the containers.

11. The method of claim 10 wherein the predetermined compression is applied by two nominally parallel movable members spaced apart from one another and arranged to hold the plurality of containers therebetween, and to move the plurality of containers along the production line without interrupting their flow while applying the predetermined compression.

12. The method of claim 11 wherein the spacing between the movable members is adjustable to allow the apparatus to operate on containers of differing sizes.

13. The method of claim 12 wherein the movable members have the form of endless belts.

14. The method of claim 13 wherein the surfaces of the endless belts which contact the plurality of containers are substantially planar and flexible.

15. The method of claim 10 further comprising detecting when one of the plurality of containers is in a predetermined position with respect to the sensor.

16. The method of claim 15 wherein the detection of the container is effected by directing a beam of light towards a container, and detecting when the beam is interrupted by, or reflected from, a container.

17. The method of claim 10 comprising detecting, in the response from the sensor assembly, the peak pressure generated within each container caused by the predetermined compression, and measuring the pressure within the container at a number of points on each side of the peak pressure.

18. The method of claim 17 further comprising generating an output signal if the peak pressure generated within each container lies outside a predetermined range.

* * * * *